United States Patent [19]

Neirinckx et al.

[11] 4,264,468
[45] Apr. 28, 1981

[54] GENERATOR FOR GALLIUM-68 AND COMPOSITIONS OBTAINED THEREFROM

[75] Inventors: Rudi D. Neirinckx, Medfield; Michael A. Davis, Westwood, both of Mass.

[73] Assignee: Massachusetts Institute of Technology, Cambridge, Mass.

[21] Appl. No.: 1,645

[22] Filed: Jan. 8, 1979

[51] Int. Cl.³ .......................... A61K 43/00; B65D 7/00
[52] U.S. Cl. ...................... 252/301.1 R; 250/432 PD; 422/61; 424/1
[58] Field of Search ..................... 424/1; 252/301.1 R; 422/61; 250/432 PD

[56] References Cited

PUBLICATIONS

Seidl, et al., Chemical Abstracts, vol. 81, 1974, Abstract No. 180245n.

Kopecky, Chemical Abstracts, vol. 86, 1977, Abstract No. 129601b.

*Primary Examiner*—Leland A. Sebastian
*Assistant Examiner*—Christine M. Nucker
*Attorney, Agent, or Firm*—Arthur A. Smith, Jr.; Paul J. Cook

[57] ABSTRACT

A generator for obtaining radioactive gallium-68 from germanium-68 bound in a resin containing unsubstituted phenolic hydroxyl groups. The germanium-68 is loaded into the resin from an aqueous solution of the germanium-68. A physiologically acceptable solution of gallium-68 having an activity of 0.1 to 50 millicuries per milliliter of gallium-68 solution is obtained. The solution is obtained from the bound germanium-68 which forms gallium-68 in situ by eluting the column with a hydrochloric acid solution to form an acidic solution of gallium-68. The acidic solution of gallium-68 can be neutralized.

8 Claims, No Drawings

GENERATOR FOR GALLIUM-68 AND COMPOSITIONS OBTAINED THEREFROM

"The Government has rights in this invention pursuant to Contract No. E(11-1)-4115 awarded by the Department of Energy."

BACKGROUND OF THE INVENTION

This invention relates to radiopharmaceutical compositions containing gallium-68 and to a generator for preparing free ionic gallium-68.

Radiochemistry presently is utilized in biological research and medical diagnosis. Certain radioactive preparations, when introduced into a biological system, will localize in specific organs, tissues or skeletal material. With radiation detecting devices such as a gamma camera or a high pressure, multiwire proportional camera, the target areas are visualized and the functioning of certain organs such as the heart, the kidney or the liver then can be monitored to diagnose a particular disease or structural defect in the biological system. Presently, the technique of tomographic reconstruction is used to obtain three-dimensional images of specific organs. These images are obtained either by utilizing an x-ray source or by administering a composition containing a photon-emitting isotope. The use of a positron-emitting isotope is preferred over the use of single photons because lower activities can be used. In addition, the use of single photons requires a collimator to obtain the desired images. The use of a positron-emitting isotope does not require the use of a collimator since they emit 2 gamma particles in directions 180° from each other rather than in random directions.

Presently, the preferred positron-emitting isotopes for use in radiopharmaceutical preparations are oxygen-15, carbon-11, nitrogen-13 and fluorine-18. Unfortunately, all of these positron-emitting isotopes have a short half-life of less than 2 hours. Because of these short half-lives, it is necessary to have an on-site cyclotron producing these isotopes. Since a cyclotron is an expensive apparatus, it would be desirable to provide a positron-emitting isotope that would be available without the need for an on-site cyclotron and which can be safely administered to humans.

It has been known that it would be desirable to obtain free gallium-68, a positron-emitting isotope, in order to provide three-dimensional images. However, prior to this invention, no practical means for obtaining gallium-68 has been available. Presently, gallium-68 is available bound with ethylenediamine tetraacetic acid (EDTA). The problem with this compound is that it is cumbersome to isolate gallium-68 from the EDTA complexant so that the gallium-68 can be bound to other molecules for diagnostic use.

SUMMARY OF THE INVENTION

This invention provides a generator for free gallium-68 and physiologically acceptable compositions containing gallium-68 which are useful in the diagnosis of a disease or a structural defect of a biological system, particularly in humans. The gallium-68 is recovered from a generator comprising germanium-68 bound to a resin containing free phenolic hydroxyl groups. The gallium-68 is eluted selectively with an acidic aqueous solution which is neutralized prior to administration.

DESCRIPTION OF SPECIFIC EMBODIMENTS

The method for obtaining germanium-68 is not critical to this invention and any conventional procedure can be utilized. For example, gallium metal is exposed to an incident proton beam in the manner described in Int. J. Appl. Radiat. Isol., Vol. 8, pp 90 to 94. High yields of the germanium-68 can be obtained which are sufficiently pure for subsequent use in forming gallium-68 solutions which can be administered to biological systems.

The purified germanium-68 solution is evaporated to dryness and then is fixed to a column containing free phenolic hydroxyl groups by first forming a solution comprising hydrogen chloride at a normality of between about 0 and 3, preferably between about 0 and 0.5 normality. This solution is percolated through the resin column in order to load the germanium-68 onto the resin. When it is desired to elute the gallium-68, an acidic solution such as hydrochloric acid is utilized. The resin utilized for this invention comprises the reaction product of an aldehyde and a polyhydroxy phenol wherein at least two hydroxyl groups are positioned adjacent on the phenyl ring. Representative suitable aldehydes include monoaldehydes such as formaldehyde, acetaldehyde or acrolein and dialdehydes such as pyrocatechol resorcinol or hydroguinone. Representative suitable phenols include pyrogallol, phloroglucinol or hydroxyquinol. The aldehyde and phenol are reacted under acid conditions. It is preferred to utilize pyrogallol and formaldehyde in an acid catalyzed reaction. Since mesh size controls the speed of the equilibrium, it is preferred to utilize small size particles having a mesh size of between about 200 and 400. The eluted gallium-68 solution then is neutralized with a basic material such as a phosphate buffer, sodium hydroxide, sodium citrate or the like to form a physiologically acceptable composition. The resultant solution of gallium-68 is physiologically acceptable, contains gallium-68 having an activity of between about 0.1 and 50 millicuries per milliliter of gallium-68 solution, preferably between about 1 and 6 millicuries, so that it can be administered to animals including humans such as by intraveneous administration.

A particularly suitable means for preparing a physiologically acceptable solution of gallium-68 is to provide the elution composition and a physiologically acceptable neutralizing composition in a kit for use in conjunction with the gallium-68 generator. For example, 1 to 3 ml of a solution comprising 0.1 N to 0.5 N hydrochloric acid can be hermetically and aseptically sealed in a container having a volume of about 1.5 to 4 ml. An additional vial which is partially evacuated is provided for the neutralizing agent for the acid such that when the eluting agent containing the gallium-68 is recovered from the germanium-68 generator, the neutralizing agent will form a solution which is preferably substantially isotonic with mammalian body fluid, e.g. human blood. The gallium-68-hydrochloric acid solution obtained from the germanium-68 generator is combined with the contents of the evacuated vial containing the neutralizing agent. This is effected conveniently by providing a needle at the bottom of the column which punctures the seal of the evacuated vial to allow the gallium-68 solution to pass into the vial. The resultant physiologically acceptable solution then can be administered to a patient, for example, by injection into the blood stream of the patient.

Conveniently, the vial containing the physiologically acceptable solution is provided with a plunger means and a means for attaching a hypodermic needle so that the vial functions as a hypodermic syringe, whereby, after preparation of the solution, the contents can be injected parenterally without being transferred to another container or syringe.

Radioactive measurements are made in the conventional manner for a period beginning after injection and lasting from about 1 minute to about 4 hours.

The following example illustrates the present invention and is not intended to limit the same.

EXAMPLE I

This example illustrates the preparation of a pharmaceutically acceptable solution of gallium-68 useful in diagnosis.

A thermosetting resin of pyrogallol and formaldehyde is formed by condensation of pyrogallol and formaldehyde under acid catalysis. The resin was placed in a column, 0.4 cm in diameter and with a height of 8 cm (minimum height 2 cm), was equilibrated with 0.3 N HCl solution and the germanium solution was eluted through the column.

In order to test for the optimum yields of gallium-68, eluting solutions were used ranging from 0 to 1 N in hydrochloric acid. All samples were counted on a NaI (Tl) well-type detector and the half-life and purity of the eluted activity determined in each case. Breakthrough of the germanium-68 parent was determined under each of the eluting conditions. High-resolution gamma-ray spectra of the eluted samples were obtained using a Ge(Li) detector.

In addition, the distribution constants ($K_D$) of germanium and gallium between the pyrogallol-formaldehyde resin and the various solutions of HCl were investigated by batch equilibration. The $K_D$ was calculated from the expression:

$$\frac{\text{Activity/g resin}}{\text{Activity/g liquid phase}}$$

The radioactive tracers used in these studies were germanium-68 and gallium-68.

The behavior of the germanium-68 adsorbed on a 1 ml column eluted with the 0.3 N HCl was determined. Up to a volume of approximately 1,000 ml, the level of germanium breakthrough, expressed as a percentage of the germanium loaded on the column, lies below the detection limit imposed by the experimental conditions ($10^{-3}$%). Table I shows the variation of germanium-68 breakthrough observed in one column volume as a function of hydrochloric acid normality.

TABLE I

VARIATION OF Ge-68 BREAKTHROUGH WITH HYDROCHLORIC ACID CONCENTRATION

| $N_{HCl}$ | % Ge-68 Breakthrough |
|---|---|
| 0 | $<10^{-3}$* |
| 0.1 | $<10^{-3}$ |
| 0.2 | $<10^{-3}$ |
| 0.3 | $<10^{-3}$ |
| 0.5 | $<10^{-3}$ |
| 1.0 | $<10^{-3}$ |

*% breakthrough = $\frac{\text{Ge-68 breakthrough/collection volume}}{\text{Ge-68 added to the column}} \times 100$

We claim:

1. The process for obtaining a physiologically acceptable aqueous solution of gallium-68 which comprises binding gallium-68 to a resin containing free phenolic hydroxyl groups wherein the phenyl group of the resin contains at least two adjacent hydroxyl groups from a dilute HCl solution whereby gallium-68 is formed in situ from germanium-68, eluting said gallium-68 from said resin with an aqueous dilute HCl solution and neutralizing the aqueous hydrochloric acid solution containing gallium-68.

2. The process of claim 1 wherein said resin is formed from pyrogallol and formaldehyde.

3. A kit for the preparation of a physiologically acceptable solution of gallium-68 from a resin column containing bound germanium-68 wherein said resin contains free phenolic hydroxyl groups and the phenyl group of the resin contains at least two adjacent hydroxyl groups which comprises a first container having a volume of about 1.5 to 4 ml in which is aseptically and hermetically sealed a 0.1 to 0.5 N HCl solution and a second container having a volume of about 3 to 10 ml and in which is sealed a neutralizing agent for said acidic solution.

4. The kit of claim 3 wherein the second container is partially evacuated.

5. The kit of claim 4 wherein the second container is provided with a hypodermic syringe.

6. A generator for gallium-68 which comprises a column of a resin containing phenyl group having at least two adjacent hydroxyl groups and germanium-68 bound to said resin.

7. The generator of claim 6 wherein said resin comprises the reaction product of an aldehyde and pyrogallol.

8. The generator of claim 7 wherein the aldehyde is formaldehyde.

* * * * *